United States Patent [19]

Frey et al.

[11] Patent Number: 4,507,503

[45] Date of Patent: Mar. 26, 1985

[54] PROCESS FOR PREPARING TERTIARY PHOSPHINES

[75] Inventors: Frederick W. Frey; John Y. Lee, both of Baton Rouge, La.

[73] Assignee: Ethyl Corporation, Richmond, Va.

[21] Appl. No.: 554,899

[22] Filed: Nov. 25, 1983

[51] Int. Cl.$^3$ .................................................. C07F 9/50
[52] U.S. Cl. ............................................ 568/17; 568/8
[58] Field of Search ...................................... 568/17, 8

[56] References Cited

U.S. PATENT DOCUMENTS

| 3,261,871 | 7/1966 | Fritzsche et al. | 568/17 |
| 3,280,195 | 10/1966 | Fritzsche et al. | 568/8 |
| 3,847,999 | 11/1974 | Gardner et al. | 568/8 |
| 4,008,282 | 2/1977 | Townsend et al. | 568/17 |
| 4,113,783 | 9/1978 | Malpass et al. | 568/17 |
| 4,131,624 | 12/1978 | Davis et al. | 568/8 |

OTHER PUBLICATIONS

Chemical Abstracts, vol. 53, 9879bc, (1959).
Chemical Abstracts, vol. 61, 8335f, (1964).
Chemical Abstracts, vol. 63, 8398h, (1965).
Kosolapoff, Organic Phosphorus Compounds, Wiley-Interscience, N.Y., vol. 1, pp. 45 to 47, (1972).

*Primary Examiner*—Helen M. S. Sneed
*Attorney, Agent, or Firm*—Donald L. Johnson; John F. Sieberth; Patricia J. Hogan

[57] ABSTRACT

Tertiary phosphine oxides, such as triphenylphosphine oxide, are reduced to the corresponding phosphines in the presence of a trialkylaluminum/trialkyl borate reducing agent.

5 Claims, No Drawings

PROCESS FOR PREPARING TERTIARY PHOSPHINES

FIELD OF INVENTION

This invention relates to a process for preparing tertiary phosphines and more particularly relates to such a process wherein a tertiary phosphine oxide is reduced to the corresponding tertiary phosphine.

BACKGROUND

It is known that tertiary phosphines are synthesizable by various techniques, including the reduction of tertiary phosphine oxides. The tertiary phosphine oxide reduction processes that have been used in the past have included the processes of U.S. Pat. Nos. 3,261,871 (Fritzche et al. I), 3,280,195 (Fritzche et al. II), 3,847,999 (Gardner et al.), 4,008,282 (Townsend et al.), 4,113,783 (Malpass et al.), and 4,131,624 (Davis et al.); Issleib et al., CA 53:9879c; Fritzche et al. III, CA 61:8335f; Koester et al., CA 63:8398h; and G. M. Kosolapoff et al., *Organic Phosphorus Compounds*, Vol. 1, Wiley Interscience Publishers (New York), 1972, pp. 45–47, as well as processes wherein the oxide has been converted to the tertiary phosphine via an intermediate.

Koester et al. teach that triphenylphosphine can be obtained in a 96.2% yield by reducing triphenylphosphine oxide with a trialkylborane at 250° C. for 5 hours. As indicated by the amounts of reactants employed, this reducing agent is inefficient and has to be used in a borane/oxide mol ratio of about 3/1 because only one of its three alkyl groups is utilized. Such a large amount of trialkylborane is economically unattractive in view of the high cost of trialkylboranes. Moreover, repetitions of the experiment of Koester et al. have shown that yields considerably lower than 96.2% are apt to be obtained in spite of this large amount of trialkylborane.

It would be advantageous to find a way of reducing tertiary phosphine oxides that would utilize less expensive and more efficient sources of the boron and alkyl moieties of a trialkylborane.

SUMMARY OF THE INVENTION

An object of this invention is to provide a novel process for reducing tertiary phosphine oxides to the corresponding phosphines.

Another object is to provide such a process which is more economical than the incorporation of a trialkylborane.

These and other objects are attained by reducing a tertiary phosphine oxide in the presence of a trialkylaluminum/trialkyl borate reducing agent.

DETAILED DESCRIPTION

Tertiary phosphine oxides utilizable in the practice of the invention are compounds corresponding to the formula:

RR'R"PO wherein R, R', and R" are independently selected from organic groups containing about 1-20 carbons. Generally the organic groups are hydrocarbonn groups, e.g., alkyl, alkenyl, cycloalkyl, cycloalkenyl, aryl, alkaryl, or aralkyl groups; and the invention is particularly useful for reducing tertiary aromatic phosphine oxides, such as triphenylphosphine oxide, tritolylphosphine oxide, etc., and tertiary aliphatic phosphine oxides, such as tributylphosphine oxide, trioctylphosphine oxide, etc., to the corresponding phosphines.

Trialkylaluminums that can be used as components of the reducing agent are generally compounds wherein the alkyl groups contain about 1-6 carbons, e.g., trimethylaluminum, triethylaluminum, tripropylaluminums, tributylaluminums, etc., although higher trialkylaluminums may be employed if desired. The use of trialkylaluminums containing different alkyl groups, e.g., methyl diethylaluminum, is within the scope of the invention; but it is generally preferred to employ a trialkylaluminum wherein the alkyl groups are the same. Triethylaluminum and triisobutylaluminum are particularly preferred. The component is suitably utilized in an amount such as to provide about one molar proportion of trialkylaluminum per molar proportion of tertiary phosphine oxide.

Trialkyl borates employable in the practice of the invention are generally compounds wherein the alkyl groups contain about 1-6 carbons, e.g. trimethyl, triethyl, tripropyl, etc., borates, with trimethyl borate being particularly preferred. This component may be used in any amount suitable for reaction with the trialkylaluminum to generate a trialkylborane in situ. However, it is an advantage of the invention that the borate can be satisfactorily used in less than an equimolar amount; and it is generally found suitable to employ about 0.04–0.5 molar proportion of borate per molar proportion of trialkylaluminum.

The reaction may be conducted in the presence or absence of a solvent. When a solvent is employed, it is usually an aliphatic or aromatic hydrocarbon, such as hexane, toluene, etc.

The temperatures employed for the reaction are temperatures effective for reduction of the oxide with the trialkylaluminum/trialkyl borate reducing agent, generally temperatures in the range of about 200°–400° C.

The following examples are given to illustrate the invention and are not intended as a limitation thereof.

EXAMPLE I

A suitable reaction vessel was charged with 25 mmols of triphenylphosphine oxide (TPPO), 10 mmols of trimethyl borate, 25 mmols of triethylaluminum, and 100 ml of n-hexane. After a preheating period of about one hour, the reaction mixture was heated at 300°–320° C. for 12 hours during which the maximum pressure was 870 psi. The reaction mixture was then cooled to room temperature and worked up to isolate 6.7 g of a crude product. VPC analysis of the product showed that the reaction resulted in a 60% conversion of TPPO and a 27.2% yield of triphenylphosphine (TPP).

EXAMPLE II

A suitable reaction vessel was charged with 5 mmols of TPPO, 2.5 mmols of trimethyl borate, and 5 mmols of triisobutylaluminum. After a 90 minute preheating period, the reaction mixture was heated at 300°–320° C. for two hours. The reaction mixture was then cooled to room temperature and worked up. Analysis showed that the reaction resulted in a 66% conversion of TPPO and an 8.6% yield of TPP.

EXAMPLE III

In a manner similar to that of Examples I and II, one molar proportion of TPPO was reacted with one molar proportion of triethylaluminum and 0.045 molar proportion of trimethyl borate in toluene at 300° C. for three hours to provide an 80% conversion of the oxide and a 76% yield of TPP.

COMPARATIVE EXAMPLE

Example III was repeated except that the trimethyl borate was eliminated from the recipe. The reaction resulted in a conversion of less than 25% of the oxide and a TPP yield of only about 5%.

EXAMPLE IV

In a similar manner, one molar proportion of trioctylphosphine oxide was reacted with one molar proportion of triethylaluminum and 0.5 molar proportion of trimethyl borate in toluene at 300° C. for three hours to provide a conversion of 32% of the oxide and a 30% yield of trioctylphosphine.

EXAMPLE V

In a similar manner, tributylphosphine oxide was reacted with one molar equivalent of triethylaluminum and 0.5 molar equivalent of distilled trimethyl borate in toluene at 300° C. to give 9% conversion of the oxide after one hour, 23% conversion after two hours, 34% conversion after three hours, and 35% conversion after four and five hours. The yields of phosphine were quantitative in each case. The reaction mixture was then cooled, and another molar equivalent of triethylaluminum was added thereto. The temperature was returned to 300° C. After three hours, the oxide conversion was 73% with a phosphine yield of 40%. After five hours, the oxide conversion was 95.4% with a phosphine yield of 59%.

EXAMPLE VI

In a similar manner, tributylphosphine oxide was reduced with one molar equivalent of triethylaluminum and 0.043 molar equivalent of trimethyl borate in toluene at 300° C. After 6 hours the oxide conversion was 55% and the tributylphosphine yield was 47%.

It is obvious that many variations can be made in the products and processes set forth above without departing from the spirit and scope of this invention.

We claim:

1. A process for producing a tertiary phosphine which comprises reacting a tertiary phosphine oxide with a trialkylaluminum/trialkyl borate reducing agent at a temperature in the range of about 200°–400° C.

2. The process of claim 1 wherein the tertiary phosphine oxide is triphenylphosphine oxide.

3. The process of claim 1 wherein the tertiary phosphine oxide is trioctylphosphine oxide.

4. The process of claim 1 wherein the tertiary phosphine oxide is tributylphosphine oxide.

5. The process of claim 1 wherein the mol ratio of trialkylaluminum to trialkyl borate is in the range of about 1/0.04–0.5.

* * * * *